(12) United States Patent
Nathanson (10) Patent No.: US 7,615,025 B2
(45) Date of Patent: Nov. 10, 2009

(54) KNEE BRACE HINGES WITH ADAPTIVE MOTION

(75) Inventor: Jeremy J. Nathanson, San Clemente, CA (US)

(73) Assignee: DJO, LLC, Vista, CA (US)

( * ) Notice: Subject to any disclaimer, the term of this patent is extended or adjusted under 35 U.S.C. 154(b) by 733 days.

(21) Appl. No.: 11/030,444

(22) Filed: Jan. 6, 2005

(65) Prior Publication Data

US 2005/0148916 A1 Jul. 7, 2005

Related U.S. Application Data

(60) Provisional application No. 60/534,719, filed on Jan. 7, 2004.

(51) Int. Cl.
*A61F 5/00* (2006.01)

(52) U.S. Cl. .......................................... 602/16; 602/26

(58) Field of Classification Search ............ 602/5, 602/16, 20–23, 26–27; 128/882
See application file for complete search history.

(56) References Cited

U.S. PATENT DOCUMENTS

| | | |
|---|---|---|
| 3,581,741 A | 6/1971 | Rosman |
| 3,779,654 A | 12/1973 | Home |
| 3,799,158 A | 3/1974 | Gardner |
| 3,817,244 A | 6/1974 | Taylor |
| 3,826,251 A | 7/1974 | Ross |
| 3,901,223 A | 8/1975 | May |
| 3,902,482 A | 9/1975 | Taylor |
| 4,241,730 A | 12/1980 | Helfet |
| 4,245,629 A | 1/1981 | Cummins |
| 4,256,097 A | 3/1981 | Willis |
| 4,320,747 A | 3/1982 | Daniell, Jr. |
| 4,337,764 A | 7/1982 | Lerman |
| 4,353,361 A | 10/1982 | Foster |
| 4,361,142 A | 11/1982 | Lewis et al. |
| 4,372,298 A | 2/1983 | Lerman |
| 4,379,463 A | 4/1983 | Meier et al. |
| 4,428,369 A | 1/1984 | Peckham et al. |
| 4,433,679 A | 2/1984 | Mauldin et al. |
| 4,463,751 A * | 8/1984 | Bledsoe ............... 602/16 |
| 4,489,718 A | 12/1984 | Martin |
| 4,493,316 A | 1/1985 | Reed et al. |
| 4,520,802 A | 6/1985 | Mercer et al. |
| 4,554,913 A | 11/1985 | Womack et al. |

(Continued)

FOREIGN PATENT DOCUMENTS

DE 40 13 693 8/1991

(Continued)

OTHER PUBLICATIONS

DonJoy (dj ortho); 1988 Bracing Catalogue; Catalog; 20 pages; 1988.

*Primary Examiner*—Michael A. Brown
(74) *Attorney, Agent, or Firm*—Ropes & Gray LLP (57) ABSTRACT

The disclosed knee brace hinges enable a knee brace including the hinges to track the natural motion of the brace wearer's knee while restraining the knee from harmful motions. In certain embodiments, in a first range of motion the hinges have only one degree of freedom, rotation about a fixed axis. In a second range of motion, the hinges have at least two degrees of freedom, rotation and translation.

16 Claims, 7 Drawing Sheets

U.S. PATENT DOCUMENTS

| | | | |
|---|---|---|---|
| 4,602,627 A | 7/1986 | Vito et al. |
| D286,183 S | 10/1986 | Womack et al. |
| 4,620,532 A | 11/1986 | Houswerth |
| 4,624,247 A | 11/1986 | Ford |
| 4,655,201 A | 4/1987 | Pirmantgen |
| 4,751,920 A | 6/1988 | Mauldin et al. |
| 4,768,500 A | 9/1988 | Mason et al. |
| 4,771,768 A | 9/1988 | Crispin |
| 4,802,467 A | 2/1989 | Pansiera |
| 4,821,707 A | 4/1989 | Audette |
| 4,856,501 A | 8/1989 | Castillo et al. |
| 4,865,024 A | 9/1989 | Hensley et al. |
| 4,928,676 A | 5/1990 | Pansiera |
| 4,940,044 A | 7/1990 | Castillo |
| 4,962,760 A | 10/1990 | Jones |
| 5,009,223 A | 4/1991 | DeFonce |
| 5,022,391 A | 6/1991 | Weidenburner |
| 5,044,360 A * | 9/1991 | Janke ............... 602/16 |
| 5,063,916 A | 11/1991 | France et al. |
| 5,074,290 A | 12/1991 | Harris et al. |
| 5,078,127 A | 1/1992 | Daneman et al. |
| 5,086,760 A | 2/1992 | Neumann et al. |
| 5,094,232 A | 3/1992 | Harris et al. |
| 5,107,824 A | 4/1992 | Rogers et al. |
| 5,230,696 A | 7/1993 | Silver et al. |
| 5,244,455 A * | 9/1993 | Swicegood et al. ........... 602/16 |
| 5,277,698 A | 1/1994 | Taylor |
| 5,292,303 A | 3/1994 | Bastyr et al. |
| 5,302,169 A | 4/1994 | Taylor |
| 5,356,370 A | 10/1994 | Fleming |
| RE34,818 E | 1/1995 | Daneman et al. |
| 5,399,149 A | 3/1995 | Frankowiak et al. |
| 5,400,806 A | 3/1995 | Taylor |
| 5,421,810 A | 6/1995 | Davis et al. |
| 5,437,619 A | 8/1995 | Malewicz et al. |
| 5,443,444 A | 8/1995 | Pruyssers |
| 5,586,970 A | 12/1996 | Morris et al. |
| 5,611,774 A | 3/1997 | Postelmans et al. |
| 5,632,725 A | 5/1997 | Silver et al. |
| 5,658,243 A | 8/1997 | Miller et al. |
| 5,792,086 A | 8/1998 | Bleau et al. |
| 5,921,946 A | 7/1999 | Tillinghast et al. |
| 6,001,075 A | 12/1999 | Clemens et al. |
| 6,074,355 A | 6/2000 | Bartlett |
| 6,309,368 B1 | 10/2001 | Herzberg et al. |
| 6,387,066 B1 | 5/2002 | Whiteside |
| 6,402,711 B1 | 6/2002 | Nauert |
| 6,793,641 B2 | 9/2004 | Freeman et al. |
| 6,953,442 B2 | 10/2005 | Yamasaki et al. |
| 6,969,364 B2 * | 11/2005 | Sterling ............... 602/16 |
| 7,044,925 B2 * | 5/2006 | Castillo et al. ............... 602/16 |
| 2004/0054311 A1 | 3/2004 | Sterling |

FOREIGN PATENT DOCUMENTS

| | | |
|---|---|---|
| EP | 0 361 405 | 4/1990 |
| WO | WO 98/14144 | 4/1998 |
| WO | WO 01/10360 A1 | 2/2001 |
| WO | WO 2004/002376 A1 | 1/2004 |

* cited by examiner

KNEE BRACE HINGES WITH ADAPTIVE MOTION

RELATED APPLICATION

This application claims priority to provisional application Ser. No. 60/534,719, filed on Jan. 7, 2004, the entire contents of which are hereby expressly incorporated by reference.

BACKGROUND OF THE INVENTION

1. Field of the Invention

The present invention relates to orthopedic braces.

2. Description of the Related Art

Many knee braces restrain the wearer's knee against harmful motions. Many of these knee braces provide such restraint while at the same time guiding the wearer's knee along a natural range of motion. Accordingly, many knee brace hinges attempt to mimic the natural motion of the knee. Some of these designs include monocentric hinges, polycentric hinges, four-bar-linkage hinges, and cam hinges. Each of these designs has a unique range of motion.

In general, when viewed in the sagittal plane, the human knee moves in a slide-and-glide fashion in which the femur partially rolls back posteriorly on the tibia as the knee flexes. The posterior roll back of the femur is most pronounced when the knee flexes beyond 90 degrees from full extension. One problem common to each of the hinge designs mentioned above is that natural knee motion varies from person to person. In fact, natural knee motion may even vary for an individual depending on the type of activity in which he or she engages. Because of these variations in natural knee motion, a knee brace may apply undesired forces to the wearer's knee as a result of the mismatch between hinge motion and natural knee motion.

Some knee brace hinge designs attempt to solve the previously mentioned problems by allowing the pivot point of the hinge to float in the anterior-posterior direction and/or the superior-inferior direction. These hinges have more than one degree of freedom and can follow more than one path of motion. The hinge pivot point is capable of changing position in order to match the instantaneous pivot point of the knee at any given time. Some examples of these types of hinges are described in U.S. Pat. Nos. 5,063,916 and 5,074,290. One drawback to these hinge designs is that the flexibility in movement renders the hinges unable to restrain some of the harmful motions to which the wearer's knee may be subjected.

In general, the knee is most vulnerable to injury when the leg is near full extension. In this position, the anterior cruciate ligament (ACL) is at its greatest tension. The ACL acts to prevent the tibia from moving anteriorly relative to the femur. To protect the ACL from injury, a knee brace restrains this type of motion (anterior movement of the tibia relative to the femur). The ACL is also vulnerable to injury from hyperextension and hyperflexion. Therefore, a given knee brace is preferably capable of limiting the degree of extension and flexion of the knee. When the knee is bent sufficiently away from full extension, the ACL becomes lax and is much less vulnerable to injury. In addition, as the knee flexes much of the anterior-posterior motion of the knee becomes controlled by muscle forces rather than ligament restraint.

A typical knee brace protects the medial and lateral collateral ligaments (MCL and LCL) by preventing varus and valgus bending of the knee. Such bending may occur from impacts to the sides of the knee.

SUMMARY OF THE INVENTION

The preferred embodiments of the present knee brace hinges with adaptive motion have several features, no single one of which is solely responsible for their desirable attributes. Without limiting the scope of these knee brace hinges as expressed by the claims that follow, their more prominent features will now be discussed briefly. After considering this discussion, and particularly after reading the section entitled "Detailed Description of the Preferred Embodiments," one will understand how the features of the preferred embodiments provide advantages, which include the ability to track natural knee motion so as to avoid applying undesired forces to the knee, while at the same time restraining the knee against harmful motions.

One embodiment of the present knee brace hinges comprises at least a first hinge plate and a cam plate. The hinge plate and the cam plate are secured to one another such that in a first range of motion the hinge plate is pivotable with respect to the cam plate but not translatable with respect thereto, and in a second range of motion the hinge plate is pivotable and translatable with respect to the cam plate.

Another embodiment of the present knee brace hinges comprises at least a first hinge plate including a pivot aperture and a guide aperture, a cam plate including a cam slot, the cam plate being secured to the hinge plate, a pivot member extending through the pivot aperture and the cam slot, and a guide member extending through the guide aperture and the cam slot. Interaction of the pivot member and guide member with the cam slot controls rotational and translational movement of the hinge plate and cam plate with respect to one another.

Another embodiment of the present knee brace hinges comprises at least a first hinge plate including a pivot aperture and a first cam slot, a cam plate including a second cam slot, the cam plate being secured to the hinge plate, a pivot member extending through the pivot aperture and the second cam slot, and a guide member secured to the cam plate and extending into the first cam slot. Interaction of the pivot member with the second cam slot and interaction of the guide member with the first cam slot controls rotational and translational movement of the hinge plate and cam plate with respect to one another.

Another embodiment of the present knee brace hinges comprises at least a first hinge plate, a cam plate including a cam slot shaped substantially as a diamond with rounded corners, the cam plate being secured to the hinge plate, and a guide member shaped substantially as an oval secured to the hinge plate and extending into the cam slot. Interaction of the guide member with the cam slot controls rotational and translational movement of the hinge plate and cam plate with respect to one another.

Another embodiment of the present knee brace hinges comprises at least a first hinge plate and at least a second hinge plate. The hinge plates are movably secured to one another such that in a first range of motion movement of the hinge plates with respect to one another includes only one degree of freedom. In a second range of motion movement of the hinge plates with respect to one another includes at least two degrees of freedom.

Another embodiment of the present knee brace hinges comprises a knee brace for supporting a wearer's knee and restraining harmful knee motions. The brace comprises at least a first rigid cuff and at least a second rigid cuff. The cuffs are movably secured to one another such that in a first range of motion movement of the cuffs with respect to one another includes only one degree of freedom. In a second range of motion movement of the cuffs with respect to one another includes at least two degrees of freedom.

Another embodiment of the present knee brace hinges comprises a method of supporting a knee in order to allow the knee to flex and extend in a natural manner, while restraining the knee against harmful motions. The method comprises the step of applying to the knee an orthopedic knee brace, the knee brace including a hinge having two states of motion, a constrained state and an adaptive state, wherein in the constrained state the hinge includes only one degree of freedom, rotation about a substantially fixed axis, and in the adaptive state the hinge includes three degrees of freedom, one rotational degree of freedom and two translational degrees of freedom.

BRIEF DESCRIPTION OF THE DRAWINGS

The preferred embodiments of the present knee brace hinges with adaptive motion, illustrating their features, will now be discussed in detail. These embodiments depict the novel and non-obvious knee brace hinges shown in the accompanying drawings, which are for illustrative purposes only. These drawings include the following figures, in which like numerals indicate like parts.

DETAILED DESCRIPTION OF THE PREFERRED EMBODIMENTS

As used herein, the term lateral means away from a vertical centerline of the body, the term medial means toward a vertical centerline of the body, the term anterior means toward the front of the body, the term posterior means toward the back of the body, the term superior means higher up on the body, and the term inferior means lower oh the body. Each of the above terms, as applied to components of the present hinges, refer to the configuration of the brace 30 shown in FIG. 1, which the brace 30 occupies when the wearer's leg is at full extension and the wearer is standing. For clarity, the wearer's leg is not illustrated.

Figure 1:
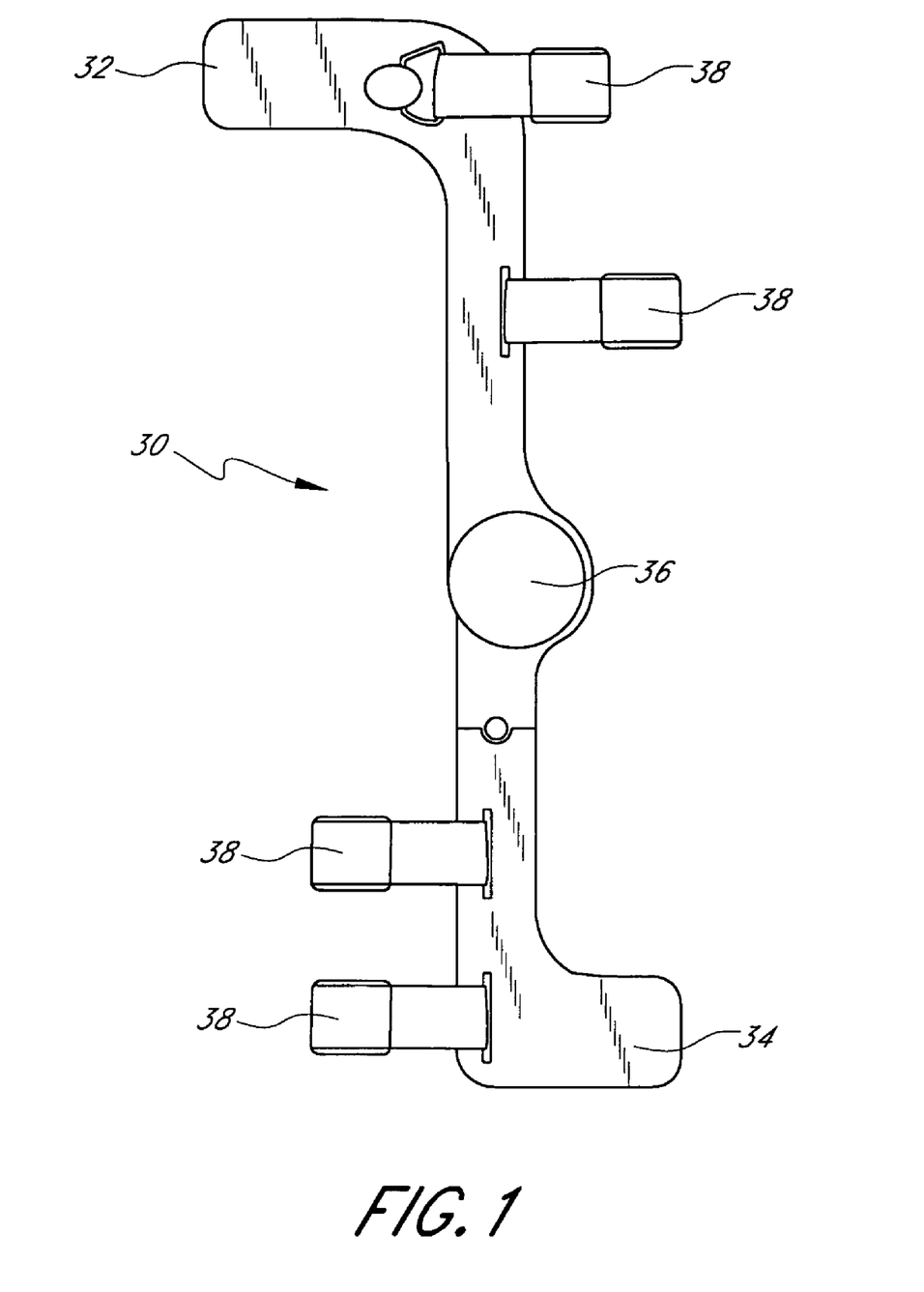
FIG. 1 is a right-side elevational view of a knee brace that is adapted to include the present knee brace hinges.

FIG. 1 illustrates an example of a knee brace 30 that is adapted to include the present knee brace hinges. The brace 30 includes a rigid thigh frame 32 and a rigid calf frame 34. A hinge 36 pivotably connects the frames 32, 34 such that the frames 32, 34 can follow the motion of their respective leg portions as the wearer's knee flexes and extends. A plurality of straps 38 helps to locate the brace 30 on the wearer's leg (not shown).

Figure 2:
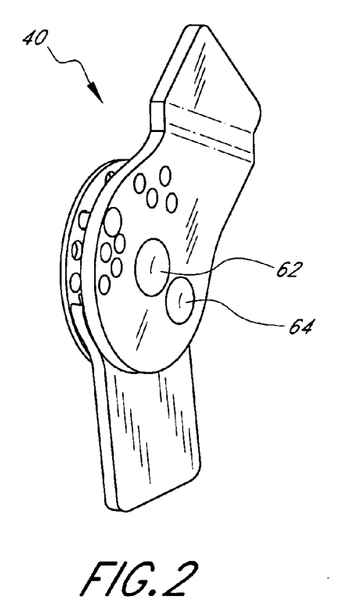
FIG. 2 is a front perspective view of one embodiment of the present knee brace hinges.
Figure 3:
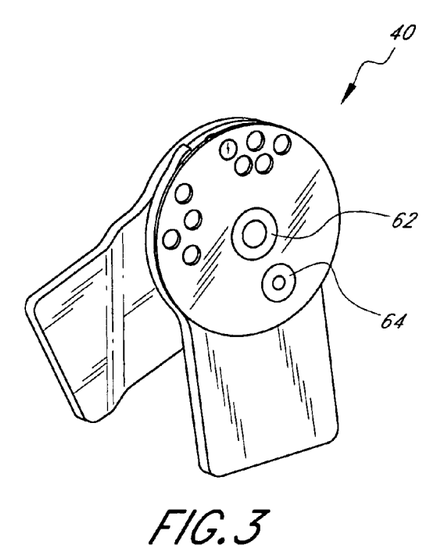
FIG. 3 is a rear perspective view of the knee brace hinge of FIG. 2.
Figures 4, 5:
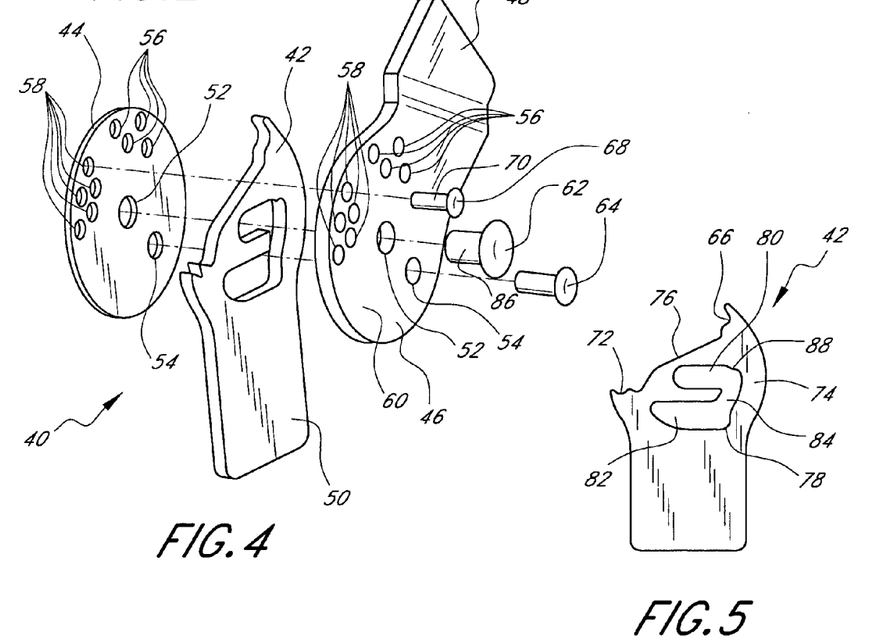
FIG. 4 is an exploded assembly view of the knee brace hinge of FIG. 2.
FIG. 5 is a right-side elevational view of the cam plate of FIG. 2.

FIGS. 2-20 illustrate various embodiments of the present knee brace hinges. With reference to FIGS. 2-4, one embodiment 40 of the present knee brace hinges comprises a plurality of moving plates. With particular reference to FIG. 4, a cammed hinge plate (cam plate) 42 is sandwiched between an inner hinge plate 44 and an outer hinge plate 46. The inner and outer plates 44, 46 pivot together with respect to the cam plate 42. An extension portion 48 of the outer plate 46 is attachable to the rigid thigh frame 32 of the knee brace 30 shown in FIG. 1. An extension portion 50 of the cam plate 42 is attachable to the rigid calf frame 34 of the knee brace 30. The hinge plates 42, 44, 46 are preferably constructed of sturdy materials, such as metals (e.g., steel or aluminum).

As used herein, the terms inner and outer refer to the position of a hinge component relative to the wearer's knee. Thus, an inner plate is adapted to be positioned relatively closer to the wearer's knee when a brace including the present hinges is worn. However, each of the illustrated hinges is adapted for use as either a medial or lateral hinge on a brace that is adapted for wear on either the right leg or the left leg. Thus, an inner plate may readily become an outer plate, and vice versa, depending upon whether the hinge is located on the medial or lateral side of the right or left leg. For simplicity, however, each of the embodiments will be described herein as if it were the medial hinge on a brace that is adapted for wear on the right leg, or as if it were the lateral hinge on a brace that is adapted for wear on the left leg. Those of skill in the art will appreciate that the positions of the inner plates and outer plates may be reversed, relative to a centerline of the wearer's body, to suit a particular application.

With continued reference to FIG. 4, in the illustrated embodiment, the inner plate 44 is circular and includes a plurality of apertures, including a pivot aperture 52, a guide member aperture, a plurality of flexion stop apertures 56 and a plurality of extension stop apertures 58. The outer plate 46 similarly includes a substantially circular portion 60 that includes a plurality of apertures, including a pivot aperture 52, a guide member aperture 54, a plurality of flexion stop apertures 56 and a plurality of extension stop apertures 58. Each aperture 52, 54, 56, 58 is adapted to receive a fastening member, such as a pin or a rivet. The positions of the apertures 52, 54, 56, 58 on the outer plate 46 correspond to the positions of the apertures 52, 54, 56, 58 on the inner plate 44. Thus, a fastening member extending through an aperture 52, 54, 56, 58 on the outer plate 46 may similarly extend through a corresponding aperture 52, 54, 56, 58 on the inner plate 44. A shaft portion of such a fastening member is adapted to engage various cammed surfaces on the cam plate 42, as described in detail below.

The pivot aperture 52 in the inner plate 44 is located at a center thereof. Similarly, the pivot aperture 52 in the outer plate 46 is located at a center of the substantially circular portion 60. A pivot member 62 extends through the pivot apertures 52 and secures the inner and outer plates 44, 46 to one another, with the cam plate 42 located in between. In the illustrated embodiment, the pivot member 62 comprises a rivet. However, those of skill in the art will appreciate that any fastening member, such as a screw or pin, could be used instead.

Figures 6, 7, 8, 9, 10:
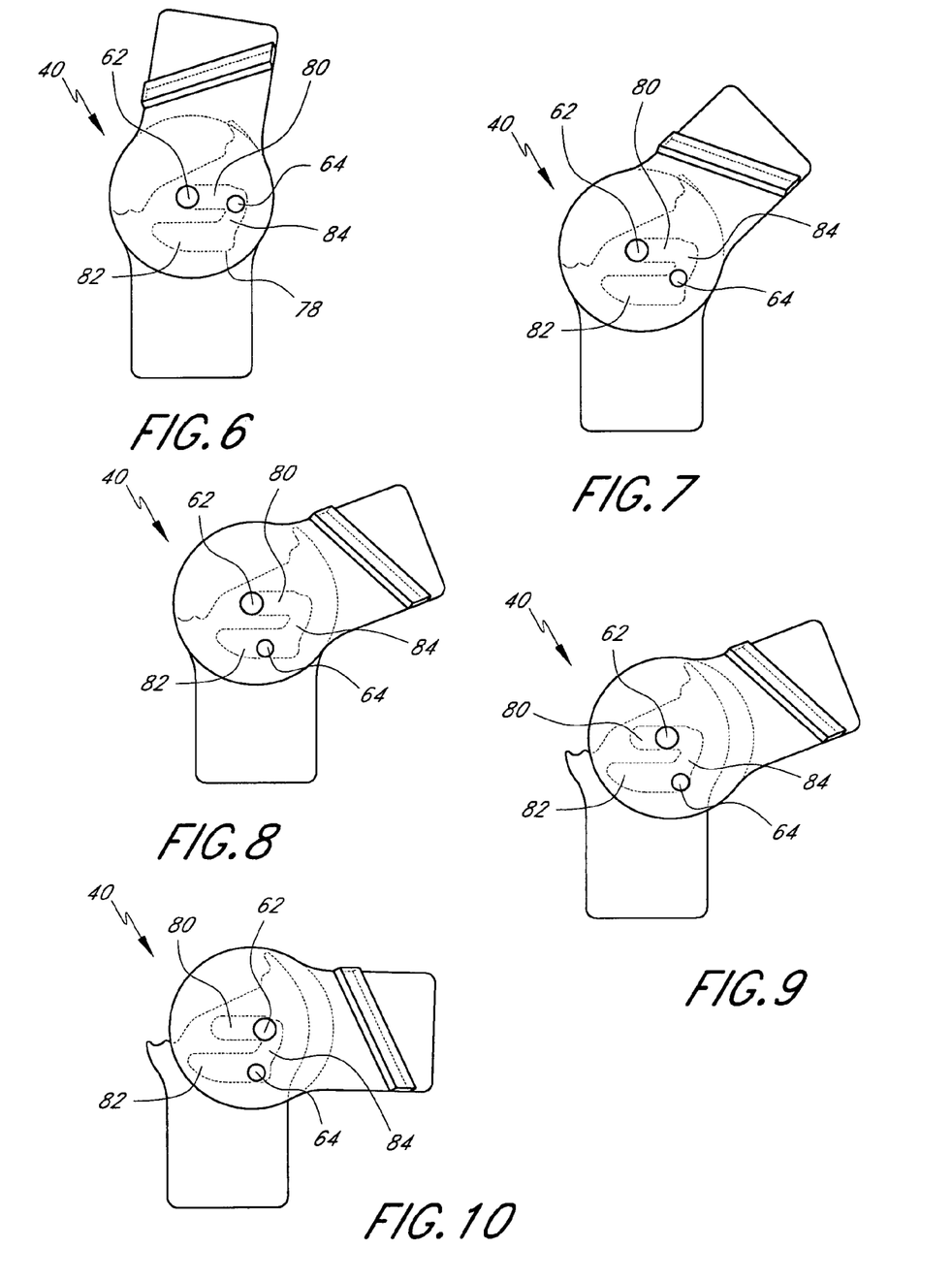
FIGS. 6-10 are right-side elevational views of the knee brace hinge of FIG. 2.

With reference to FIGS. 4 and 6, the guide member aperture 54 in each of the inner and outer plates 44, 46 is located approximately directly posterior of the respective pivot aperture 52 when the hinge is at full extension, and approximately halfway between the pivot aperture 52 and the posterior edge of the respective plate 44, 46. A guide member 64 extends through the guide member apertures 54. The guide member 64 guides the motion of the hinge 40, as described in detail below. In the illustrated embodiment, the guide member 64 comprises a rivet. However, those of skill in the art will appreciate that any fastening member, such as a screw or pin, could be used instead.

With reference to FIGS. 2 and 4, the flexion stop apertures 56 in each of the plates 44, 46 are located near an edge of each plate 44, 46, anterior and superior to the pivot aperture 52 when the hinge 40 is at full extension. In the illustrated embodiment, four flexion stop apertures 56 are provided. Those of skill in the art will appreciate, however, that fewer or more flexion stop apertures 56 could be provided. The extension stop apertures 58 in each of the plates are located near an edge of each plate, anterior and inferior relative to the pivot aperture 52 when the hinge is at full extension. In the illustrated embodiment, five extension stop apertures 58 are provided. Those of skill in the art will appreciate, however, that fewer or more extension stop apertures 58 could be provided.

Each of the flexion stop apertures 56 is adapted to receive a flexion stop member (not shown). The flexion stop member extends through corresponding flexion stop apertures 56 on each of the inner and outer plates 44, 46. A shaft portion of the flexion stop member is adapted to engage a flexion stop surface 66 (FIG. 5) on the cam plate 42 in order to limit the maximum flexion angle that the hinge 40 can achieve, as described in detail below. Each of the extension stop apertures 58 is adapted to receive an extension stop member 68 (FIG. 4). The extension stop member 68 extends through corresponding extension stop apertures 58 on each plate. A shaft portion 70 of the extension stop member 68 is adapted to engage an extension stop surface 72 (FIG. 5) on the cam plate 42 in order to limit the maximum extension angle that the hinge 40 can achieve, as described in detail below.

With reference to FIGS. 4 and 5, in the illustrated embodiment, the cam plate 42 includes a substantially semi-circular portion 74 that is contiguous with the extension portion. The semi-circular portion 74 includes smoothly rounded edges that terminate in a substantially crescent-shaped cammed surface 76. The cammed surface 76 includes a substantially straight central portion that runs diagonally with respect to a longitudinal axis of the cam plate 42. Opposite ends of the central portion terminate in undulating portions that provide a plurality of flexion stop surfaces 66 and extension stop surfaces 72. The flexion stop member is adapted to contact one of the flexion stop surfaces 66. The flexion stop surface 66 contacted depends upon which of the flexion stop apertures 56 contains the flexion stop member. When the flexion stop contacts one of the flexion stop surfaces 66, the brace 30 is restrained against further flexion. Similarly, the extension stop member 68 is adapted to contact one of the extension stop surfaces 72. The extension stop surface 72 contacted depends upon which of the extension stop apertures 58 contains the extension stop member 68. When the extension stop member 68 contacts one of the extension stop surfaces 72, the brace 30 is restrained against further extension.

The positions of the flexion stop apertures 56 and the shapes of the flexion stop surfaces 66 determine the maximum flexion angles for the brace 30. For example, the brace 30 may have maximum flexion angles at 30°, 45°, 60° and 75° of flexion. Similarly, the positions of the extension stop apertures 58 and the shapes of the extension stop surfaces 72 determine the maximum extension angles for the brace 30. For example, the brace 30 may have maximum extension angles at 0°, −15°, −30°, −45° and −60° of extension.

With reference to FIG. 5, an interior region of the semi-circular portion 74 includes a cam slot 78. In the illustrated embodiment, the cam slot 78 is substantially U-shaped and comprises an upper horizontal slot 80, a lower horizontal slot 82 and a diagonal slot 84 connecting posterior ends of the upper and lower horizontal slots 80, 82. A width of the upper slot 80 is substantially identical to a width of the shaft portion 86 (FIG. 4) of the pivot member 62. The upper slot 80 is thus adapted to slidably receive the pivot member 62. A posterior portion of a superior wall of the upper slot 80 includes a protruding bulge 88. The bulge 88 limits the posterior sliding movement of the pivot member 62, as explained in detail below.

With reference to FIGS. 6-10, the upper horizontal slot 80 is adapted to receive the pivot member 62, and the diagonal slot 84 and the lower horizontal slot 82 are adapted to receive the guide member 64. The hinge 40 has two states of motion, and the pivot member 62 and guide member 64 determine the characteristics of each state of motion. The first state, illustrated in FIGS. 6 and 7, is referred to as the constrained state. The hinge 40 occupies this state from full extension to a predetermined flexion angle at which the second state begins. This angle, referred to as the transition angle, may be in the range from about 45° to about 60°. Near the transition angle, the risk of injury to the ACL is greatly reduced. Also, variations in knee motion across different brace 30 wearers become increasingly pronounced.

In the human knee, motion of the knee near full extension is generally limited to rotation around a nearly fixed axis. Therefore, in the illustrated embodiment the constrained state provides the hinge 40 with only one degree of freedom. This degree of freedom is angular rotation about the pivot member 62. However, in alternative embodiments translation of the pivot member 62 may be coupled to the rotation of the hinge 40 in order to match the natural motion of a given wearer's knee.

The interaction of the pivot member 62 and guide member 64 with the cam slot 78 (FIGS. 6 and 7) limits the hinge 40 to rotation around a nearly fixed axis in the constrained state. The upper slot 80 constrains the pivot member 62 against translation in every direction except the posterior direction. Contact between the guide member 64 and a posterior wall of the diagonal slot 84 constrains the pivot member 62 against translation in the posterior direction. Thus, the only degree of freedom available to the hinge 40 is rotation about the pivot member 62 as the guide member 64 slides along the posterior wall of the diagonal slot 84. Because this rotation is the only degree of freedom available to the hinge 40, in the constrained state the hinge 40 restrains the knee from harmful motions, such as anterior-posterior translation, varus and valgus bending, and hyperextension. The hinge 40 thus protects the wearer's ACL, MCL and LCL from damage.

The second state of motion, illustrated in FIGS. 8-10, is referred to as the adaptive state or the floating state. This state begins when the knee flexes past the transition angle, which occurs around the time that the guide member 64 moves from the diagonal slot 84 into the lower horizontal slot 82. Once the guide member 64 exits the diagonal slot 84, a gap opens between the guide member 64 and the posterior wall of the diagonal slot 84. The guide member 64 thus no longer completely constrains the pivot member 62 against translation in the posterior direction. Thus, in the adaptive state the pivot member 62 is slidable in the anterior-posterior direction within the upper horizontal slot 80. This movement of the pivot member 62 tracks the translating center of knee rotation as the femur slides on the tibia so that the hinge matches the natural motion of the brace wearer's knee. However, interaction of the guide member 64 and the walls of the cam slot 78 still provides a limit on the posterior movement of the pivot member 62 within the upper horizontal slot 80. Further, even in the adaptive state the hinge 40 still maintains restraint against varus and valgus bending as well as hyperflexion. The pivot member 62 is slidable in the posterior direction within the upper horizontal slot 80 until it contacts the bulge 88. The bulge 88 narrows the slot 80 such that the pivot member 62 cannot pass. The hinge 40 can continue to rotate about the pivot member 62 until the guide member 64 contacts the superior wall of the lower slot 82. When this contact occurs, the hinge 40 is at its maximum flexion angle. This maximum flexion angle prevents the wearer's knee from hyperflexing.

Figure 11:
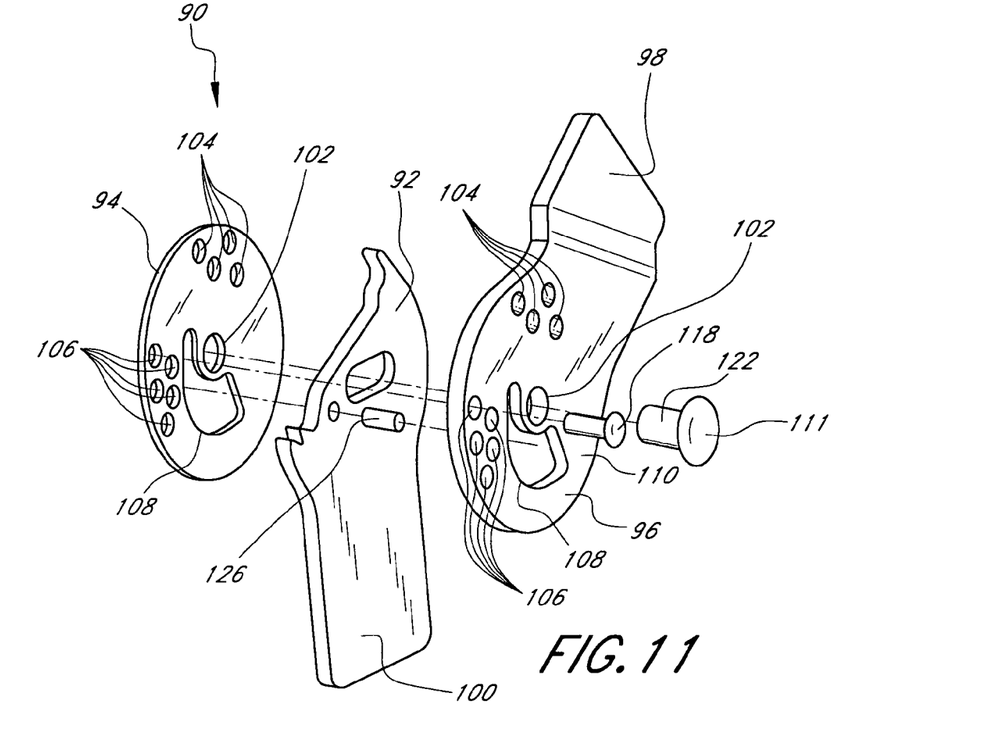
FIG. 11 is an exploded assembly view of another embodiment of the present knee brace hinges.

FIGS. 11-15 illustrate another embodiment of the present knee brace hinges with adaptive motion. Like the hinge 40 of FIGS. 2-10, the hinge 90 comprises a plurality of moving plates (FIG. 11). A cammed hinge plate (cam plate) 92 is sandwiched between an inner hinge plate 94 and an outer hinge plate 96. The inner and outer plates 94, 96 pivot together with respect to the cam plate 92. An extension portion 98 of the outer plate 96 is attachable to the rigid thigh frame 32 of the knee brace 30 shown in FIG. 1. An extension portion 100 of the cam plate 92 is attachable to the rigid calf frame 34 of the knee brace 30. The hinge plates 92, 94, 96 are preferably constructed of sturdy materials, such as metals (e.g., steel or aluminum).

With particular reference to FIG. 11, in the illustrated embodiment the inner plate 94 is circular and includes a plurality of apertures, including a pivot aperture 102, a plurality of flexion stop apertures 104 and a plurality of extension stop apertures 106. The inner plate 94 further includes a cam slot 108. The outer plate 96 similarly includes a substantially circular portion 110 that includes a plurality of apertures, including a pivot aperture 102, a plurality of flexion stop apertures 104, a plurality of extension stop apertures 106 and a cam slot 108. Each aperture 102, 104, 106 is adapted to receive a fastening member, such as a pin or a rivet. The positions of the apertures 102, 104, 106 and the cam slot 108 on the outer plate 96 correspond to the positions of the apertures 102, 104, 106 and the cam slot 108 on the inner plate 94. Thus, a fastening member extending through an aperture 102, 104, 106 or cam slot 108 on the outer plate 96 may similarly extend through a corresponding aperture 102, 104, 106 or cam slot 108 on the inner plate 94. A shaft portion of a fastening member that extends through one of the apertures is adapted to engage various cammed surfaces on the cam plate 92, as described in detail below.

With further reference to FIG. 11, the pivot aperture 102 in the inner plate 94 is located at a center thereof. Similarly, the pivot aperture 102 in the outer plate 96 is located at a center of the substantially circular portion 110. A pivot member 111 extends through the pivot apertures 102 and secures the inner and outer plates 94, 96 to one another, with the cam plate 92 located in between. In the illustrated embodiment, the pivot member 111 comprises a rivet. However, those of skill in the art will appreciate that any fastening member, such as a screw or pin, could be used instead.

Figure 13:
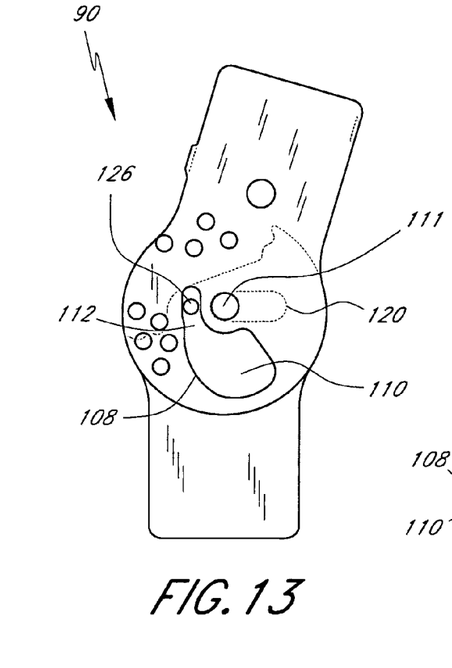
FIGS. 13-15 are right-side elevational views of the knee brace hinge of FIG. 11.
Figure 14:
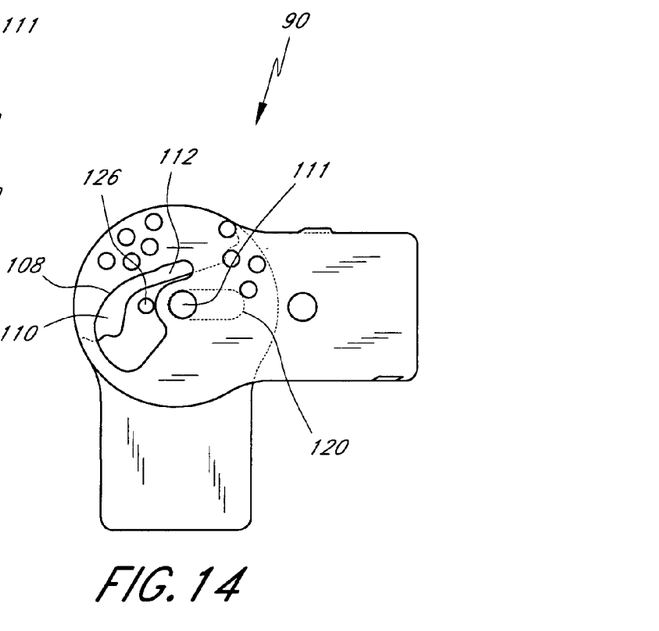
Figure 15:
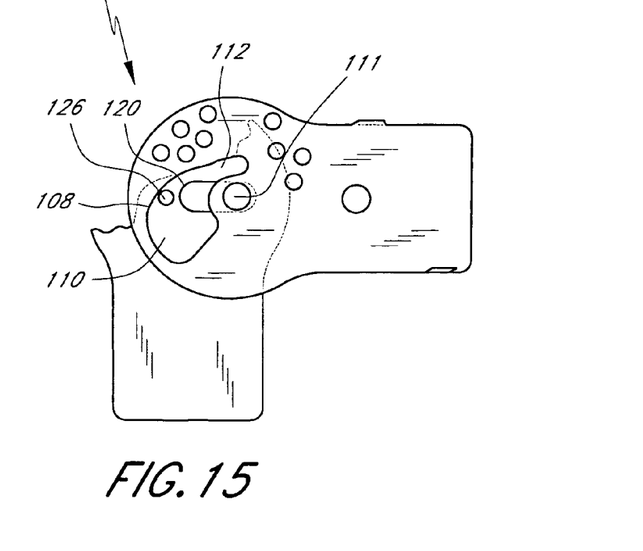

With reference to FIGS. 13-15, the cam slot 108 in each of the inner and outer plates 94, 96 includes an enlarged main portion 110 with an extending panhandle portion 112. When the hinge 90 is at full extension (FIG. 13), an upper extent of the panhandle portion 112 is located anterior of the pivot aperture 102. The remainder of the panhandle portion 112 extends inferior and posterior therefrom, and joins the enlarged main portion 110, which is located inferior and posterior of the pivot aperture 102 when the hinge 90 is at full extension.

Figure 12:
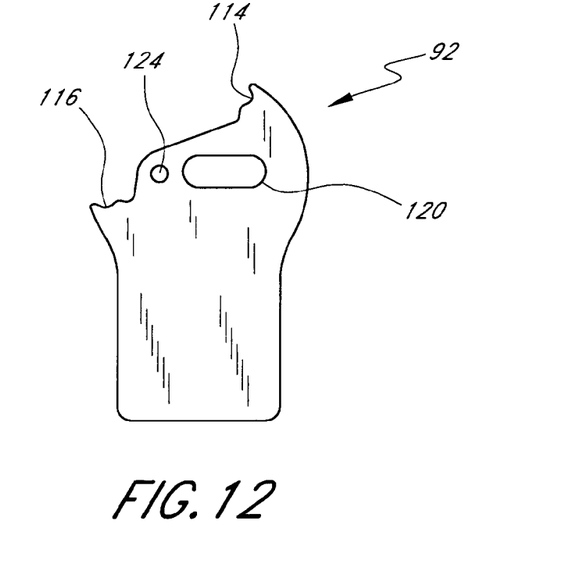
FIG. 12 is a right-side elevational view of the cam plate of FIG. 11.

With reference to FIG. 12, in the illustrated embodiment, the perimeter shape of the cam plate 92 is substantially identical to the perimeter shape of the cam plate 42 illustrated in FIG. 5. The cam plate 92 thus includes flexion stop surfaces 114 and extension stop surfaces 116. With reference to FIG. 11, in the illustrated embodiment, the inner and outer plates 94, 96 include flexion stop apertures 104 and extension stop apertures 106 that are substantially identical to their counterparts in the hinge 40 of FIGS. 2-10. The hinge 90 further optionally includes a flexion stop member (not shown) and an extension stop member 118. Thus, the hinge 90 of FIGS. 11-15 is adapted to provide the brace wearer with a range of maximum flexion and extension angles in the same manner as the hinge 40 of FIGS. 2-10.

With further reference to FIG. 12, an interior region of the cam plate 92 includes a cam slot 120. In the illustrated embodiment, the cam slot 120 is substantially oval-shaped and horizontal when the hinge 90 is at full extension. A width of the cam slot 120 is substantially identical to a width of the shaft portion 122 (FIG. 11) of the pivot member 111. The cam slot 120 is thus adapted to slidably receive the pivot member 111.

The cam plate 92 further includes an aperture 124 that is located anterior of the cam slot 120. The aperture 124 receives a guide member 126 (FIG. 11), which in the illustrated embodiment comprises a cylindrical pin. The guide member 126 protrudes from both surfaces of the cam plate 92. Opposite ends of the guide member 126 are thus adapted to engage the cam slots 108 in the inner and outer plates 94, 96. The guide member 126 guides the motion of the hinge 90, as described in detail below. In the illustrated embodiment, the guide member 126 comprises a pin. However, those of skill in the art will appreciate that any fastening member, such as a screw or rivet, could be used instead.

With reference to FIGS. 13-15, the cam slot 120 in the cam plate 92 is adapted to receive the pivot member 111, and the cam slots 108 in the inner and outer plates 94, 96 are adapted to receive the guide member 126. Like the hinge 40 described above and illustrated in FIGS. 2-10, the hinge 90 of FIGS. 11-15 has two states of motion, and the pivot member 111 and guide member 126 determine the characteristics of each state of motion. The first state (the constrained state) is illustrated in FIG. 13. The hinge 90 occupies the constrained state from full extension to a predetermined flexion angle at which the second state begins. This angle (the transition angle) may be in the range from about 45° to about 60°.

In the illustrated embodiment, the constrained state provides the hinge 90 with only one degree of freedom. This degree of freedom is angular rotation about the pivot member 111. However, in alternative embodiments translation of the pivot member 111 may be coupled to the rotation of the hinge 90 in order to match the natural motion of a given wearer's knee.

The interaction of the pivot member 111 with the cam slot 120 in the cam plate 92, and the interaction of the guide member 126 with the cam slots 108 in the inner and outer plates 94, 96 (FIG. 13) limits the hinge 90 to rotation around a nearly fixed axis in the constrained state. The cam slot 120 in the cam plate 92 constrains the pivot member 111 against translation in every direction except the posterior direction. Contact between the guide member 126 and an anterior wall of the cam slots 108 in the inner and outer plates 94, 96 constrains the pivot member 111 against translation in the posterior direction. Thus, the only degree of freedom available to the hinge 90 is rotation about the pivot member 111 as the guide member 126 slides along the anterior wall of the cam slots 108. Because this rotation is the only degree of freedom available to the hinge 90, in the constrained state the hinge 90 restrains the knee from harmful motions, such as anterior-posterior translation, varus and valgus bending, and hyperextension. Thus, the hinge 90 protects the wearer's ACL, MCL and LCL from damage.

The second state of motion (the adaptive state or the floating state) is illustrated in FIGS. 14 and 15. This state begins when the knee flexes past the transition angle, which occurs around the time that the guide member 126 enters the enlarged main portion 110 of the cam slots 108 in the inner and outer plates 94, 96. Once the guide member 126 enters this portion 110, gaps may develop between the guide member 126 and the walls of the main portion 110. The guide member 126 thus no longer completely constrains the pivot member 111 against translation in the posterior direction. Thus, in the adaptive state the pivot member 111 is slidable in the anterior-posterior direction within the cam slot 120 in the cam plate 92. This movement of the pivot member 111 tracks the translating center of knee rotation as the femur slides on the tibia so that the hinge 90 matches the natural motion of the brace wearer's knee. However, interaction of the guide member 126 and the walls of the cam slots 108 in the inner and outer plates 94, 96 still provides a limit on the posterior movement of the pivot member 111 within the cam slot 120 in the cam plate 92. Further, even in the adaptive state the hinge 90 still maintains restraint against varus and valgus bending as well as hyperflexion.

Figure 16:
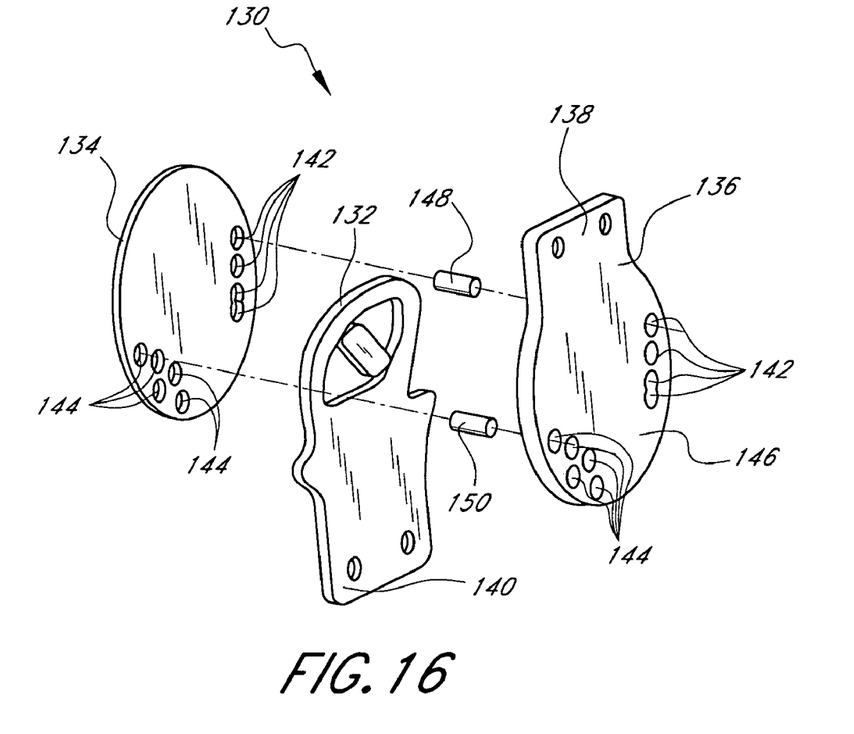
FIG. 16 is an exploded assembly view of another embodiment of the present knee brace hinges.

FIGS. 16-20 illustrate another embodiment of the present knee brace hinges with adaptive motion. Like the hinges 40, 90 of FIGS. 2-16, the hinge 130 comprises a plurality of moving plates (FIG. 16). A cammed hinge plate (cam plate) 132 is sandwiched between an inner hinge plate 134 and an outer hinge plate 136. The inner and outer plates 136 pivot together with respect to the cam plate 132. An extension portion 138 of the outer plate 136 is attachable to the rigid thigh frame 32 of the knee brace 30 shown in FIG. 1. An extension portion 140 of the cam plate 132 is attachable to the rigid calf frame 34 of the knee brace 30. The hinge plates 132, 134, 136 are preferably constructed of sturdy materials, such as metals (e.g., steel or aluminum).

Figures 18, 19, 20:
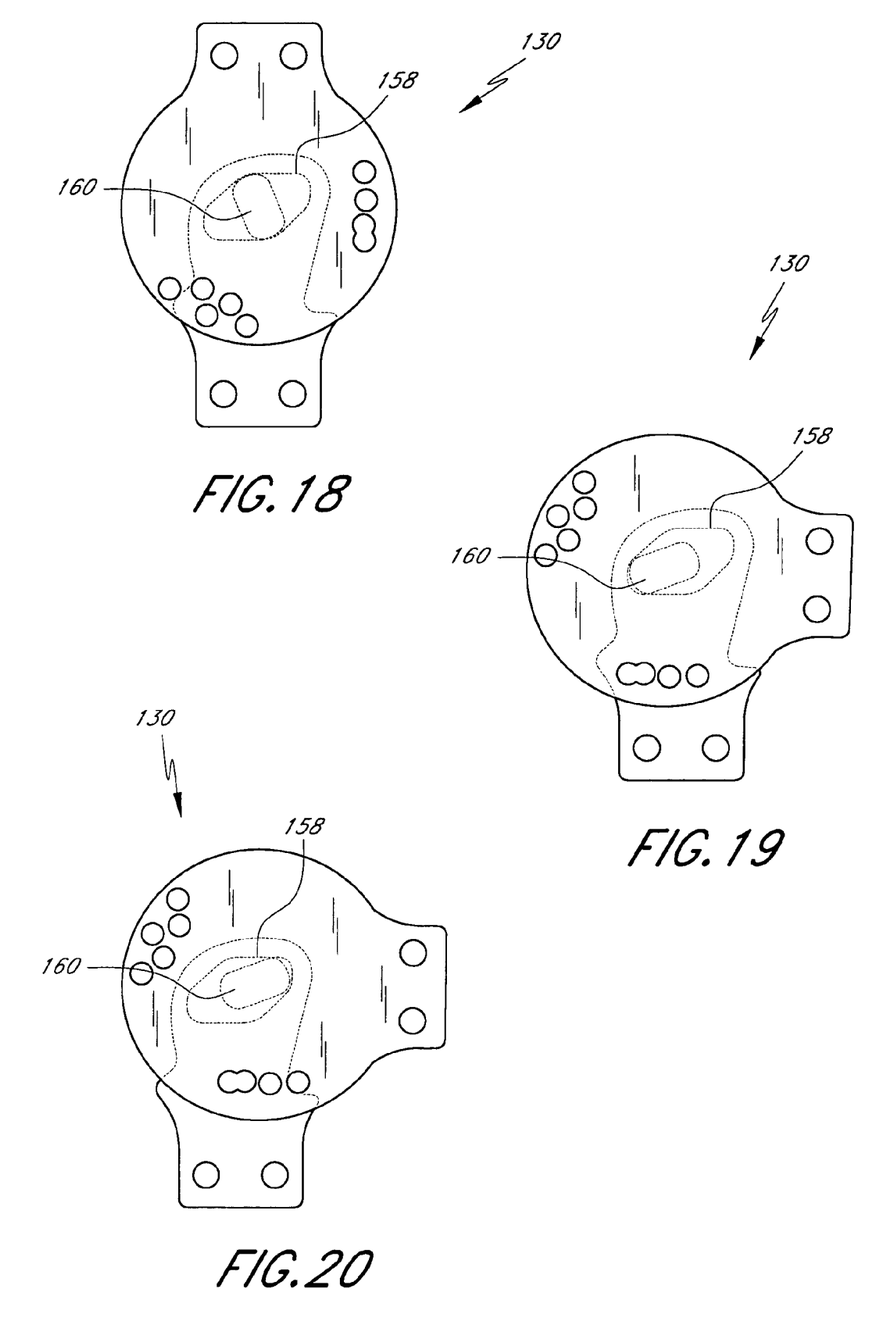
FIGS. 18-20 are right-side elevational views of the knee brace hinge of FIG. 16.

With reference to FIG. 16, in the illustrated embodiment the inner plate 134 is circular and includes a plurality of flexion stop apertures 142 and a plurality of extension stop apertures 144. The outer plate 136 similarly includes a substantially circular portion 146 that includes a plurality of flexion stop apertures 142, and a plurality of extension stop apertures 144. The flexion stop apertures 142 in each of the plates are located near an edge of each plate, in a posterior region thereof when the hinge 130 is at full extension (FIG. 18). In the illustrated embodiment, four flexion stop apertures 142 are provided. Those of skill in the art will appreciate, however, that fewer or more flexion stop apertures 142 could be provided. The extension stop apertures 144 in each of the plates 134, 136 are located near an edge of each plate 134, 136, in an anterior/inferior region thereof when the hinge 130 is at full extension (FIG. 18). In the illustrated embodiment, five extension stop apertures 144 are provided. Those of skill in the art will appreciate, however, that fewer or more extension stop apertures 144 could be provided.

Each flexion stop aperture 142 is adapted to receive a flexion stop member 148, and each extension stop aperture 144 is adapted to receive an extension stop member 150. In the illustrated embodiment, the stop members 148, 150 comprise pins. The positions of the flexion stop apertures 142 on the outer plate 136 correspond to the positions of the flexion stop apertures 142 on the inner plate 134, and the positions of the extension stop apertures 144 on the outer plate 136 correspond to the positions of the extension stop apertures 144 on the inner plate 134. Thus, a flexion stop member 148 extending through an aperture 142, 144 on the outer plate 136 may similarly extend through a corresponding aperture 142, 144 on the inner plate 134, and an extension stop member 150 extending through an aperture 142, 144 on the outer plate 136 may similarly extend through a corresponding aperture 142, 144 on the inner plate 134. The flexion stop member 148 is adapted to engage a flexion stop surface 152 (FIG. 17) on the cam plate 132, and the extension stop member 150 is adapted to engage an extension stop surface 154 on the cam plate 132. The stop members 148, 150 and stop surfaces 152, 154 limit the flexion and extension of the hinge 130 in a manner similar to that described above with respect to the hinges 40, 90 of FIGS. 2-15.

Figure 17:
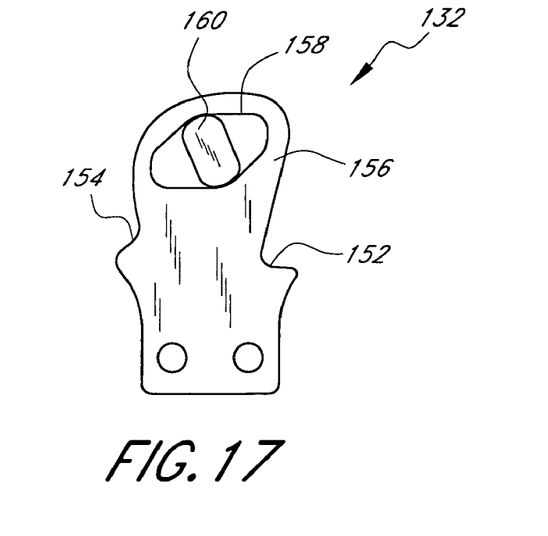
FIG. 17 is a right-side elevational view of the cam plate of FIG. 16.

With reference to FIG. 17, the cam plate 132 includes an oblong portion 156 having a cam slot 158 in a superior region thereof. A posterior surface at the base of the oblong portion includes a shoulder that provides the flexion stop surface 152. An anterior surface at the base of the oblong portion includes a shoulder that provides the extension stop surface 154. The cam slot 158 is shaped substantially as a diagonally oriented diamond with rounded corners.

A guide member 160 is movable within the cam slot 158. Interaction between the guide member 160 and walls of the cam slot 158 guides the motion of the hinge 130, as described in detail below. In the illustrated embodiment, the guide member 160 is shaped as a flat plate having an oval perimeter. The guide member 160 is secured to both of the inner and outer plates 134, 136 so as not to be movable relative to either plate. For example, the guide member 160 may be formed integrally with one of these plates 134, 136 and secured to the other plate 134, 136, or formed as a separate piece and secured to both plates 134, 136. Welds or adhesive, for example, may secure the guide member 160 to one or both plates 134, 136.

With reference to FIGS. 18-20, the cam slot 158 in the cam plate 132 is adapted to receive the guide member 160. Like the hinges 40, 90 described above and illustrated in FIGS. 2-15, the hinge 130 of FIGS. 16-20 has two states of motion, and the guide member 160 determines the characteristics of each state of motion. The first state (the constrained state) is illustrated in FIG. 18. The hinge 130 occupies the constrained state from full extension to a predetermined flexion angle at which the second state begins. This angle (the transition angle) may be in the range from about 45° to about 60°.

In the illustrated embodiment, the constrained state provides the hinge 130 with only one degree of freedom. This degree of freedom is angular rotation about the guide member 160. However, in alternative embodiments translation of the guide member 160 may be coupled to the rotation of the hinge 130 in order to match the natural motion of a given wearer's knee.

The interaction of the guide member 160 with the cam slot 158 (FIG. 18) limits the hinge 130 to rotation around a nearly fixed axis in the constrained state. At full extension, a longitudinal axis of the guide member 160 is substantially aligned with a minor axis of the diamond-shaped cam slot 158. From this orientation, and as the inner and outer plates 134, 136 pivot with respect to the cam plate 132, contact between ends of the guide member 160 and walls of the cam slot 158 constrain the guide member 160 against translation in every direction. Thus, the only degree of freedom available to the hinge 130 is rotation about the guide member 160 as the guide member 160 twists within the cam slot 158. Because this rotation is the only degree of freedom available to the hinge 130, in the constrained state the hinge 130 restrains the knee from harmful motions, such as anterior-posterior translation, varus and valgus bending, and hyperextension.

The second state of motion (the adaptive state or the floating state) is illustrated in FIGS. 19 and 20. This state begins when the knee flexes past the transition angle, which occurs around the time that opposite ends of the guide member 160 no longer contact opposite walls of the cam slot 158. Once the guide member 160 reaches this orientation, gaps between the guide member 160 and the walls of the cam slot 158 enable the guide member 160 to translate in all directions. Thus, in the adaptive state the pivot member is rotatable and translatable within the cam slot 158 (FIGS. 19 and 20). This movement of the guide member 160 allows the pivot axis of the hinge 130 to track the translating center of knee rotation as the femur slides on the tibia so that the hinge 130 matches the natural motion of the brace wearer's knee. However, interaction of the guide member 160 and the walls of the cam slot 158 still provides limits on the movement of the guide member 160 within the cam slot 158. The hinge 130 thus enables the brace 30 to provide restraint against those motions that may harm the knee, such as varus and valgus bending and hyperflexion.

As the above description illustrates, the embodiments of the present knee brace hinges 40, 90, 130 advantageously restrain anterior-posterior motion of the wearer's femur relative to his or her tibia when the hinges are at full extension. At full extension, certain components of the knee (such as the ACL) are most vulnerable to injury. When the knee is sufficiently flexed so as to put the knee components in a less vulnerable position, the hinges transition into a state that allows anterior-posterior motion of the femur relative to the tibia. The hinges thus provide little or no restraint against natural knee motion at flexion angles where the knee is relatively less vulnerable.

SCOPE OF THE INVENTION

The above presents a description of the best mode contemplated for carrying out the present knee brace hinges with adaptive motion, and of the manner and process of making and using them, in such full, clear, concise, and exact terms as to enable any person skilled in the art to which it pertains to make and use these knee brace hinges. These knee brace hinges are, however, susceptible to modifications and alternate constructions from that discussed above that are fully equivalent. Consequently, these knee brace hinges are not limited to the particular embodiments disclosed. On the contrary, these knee brace hinges cover all modifications and alternate constructions coming within the spirit and scope of the knee brace hinges as generally expressed by the following claims, which particularly point out and distinctly claim the subject matter of the knee brace hinges.

What is claimed is:

1. A hinge adapted for use in a knee brace, comprising:
   at least a first hinge plate including a pivot aperture and a guide aperture;
   a cam plate including a cam slot, the cam plate being secured to the hinge plate;
   a pivot member extending though the pivot aperture and the cam slot; and
   a guide member extending though the guide aperture and the cam slot;
   wherein interaction of the pivot member and guide member with the cam slot controls rotational and translational movement in an anterior-posterior direction of the hinge plate and cam plate with respect to one another.

2. The hinge of claim 1, wherein the cam slot includes an upper horizontal portion, a lower horizontal portion and a diagonal portion connecting the horizontal portions.

3. The hinge of claim 2, wherein the pivot member is disposed in the upper horizontal portion, and the guide member is disposed in either the diagonal portion or the lower horizontal portion.

4. The hinge of claim 2, wherein in a first range of motion interaction between the guide member and the cam slot restrains the pivot member from translation within the upper horizontal portion.

5. The hinge of claim 4, wherein in a second range of motion the pivot member is translatable within the upper horizontal portion.

6. The hinge of claim 1, further comprising a second hinge plate including a pivot aperture and a guide aperture, the cam plate being sandwiched between the first and second hinge plates.

7. The hinge of claim 1 in combination with a knee brace.

8. A hinge adapted for use in a knee brace, comprising:
   at least a first hinge plate including a pivot aperture and a first cam slot, wherein the first cam slot includes an enlarged main portion and a panhandle portion;
   a cam plate including a second cam slot, the cam plate being secured to the hinge plate;
   a pivot member extending though the pivot aperture and the second cam slot; and
   a guide member secured to the cam plate and extending into the first cam slot;
   wherein interaction of the pivot member with the second cam slot and interaction of the guide member with the first cam slot controls rotational and translational movement in an anterior-posterior direction of the hinge plate and cam plate with respect to one another.

9. The hinge of claim 8, wherein the second cam slot is substantially oval shaped.

10. The hinge of claim 8, wherein in a first range of motion interaction between the guide member and the first cam slot restrains the pivot member from translation within the second cam slot.

11. The hinge of claim 10, wherein in a second range of motion the pivot member is translatable within the second cam slot.

12. The hinge of claim 8, further comprising a second hinge plate including a pivot aperture and a guide aperture, the cam plate being sandwiched between the first and second hinge plates.

13. The hinge of claim 8 in combination with a knee brace.

14. A hinge adapted for use in a knee brace, comprising:
   at least a first hinge plate;
   a cam plate including a cam slot shaped substantially as a diamond with rounded corners, the cam plate being secured to the hinge plate; and
   a guide member shaped substantially as an oval secured to the hinge plate and extending into the cam slot;
   wherein interaction of the guide member with the cam slot controls rotational and translational movement in an anterior-posterior direction of the hinge plate and cam plate with respect to one another.

15. The hinge of claim 14, wherein in a first range of motion opposite ends of the guide member contact walls of the cam slot, thereby restraining the guide member from translation within the cam slot.

16. The hinge of claim 15, wherein in a second range of motion gaps between the opposite ends of the guide member and the walls of the cam slot enable the guide member to translate within the cam slot.

* * * * *

UNITED STATES PATENT AND TRADEMARK OFFICE
CERTIFICATE OF CORRECTION

PATENT NO.           : 7,615,025 B2                                    Page 1 of 1
APPLICATION NO. : 11/030444
DATED                    : November 10, 2009
INVENTOR(S)         : Jeremy Nathanson

It is certified that error appears in the above-identified patent and that said Letters Patent is hereby corrected as shown below:

Claim 1, column 11, lines 57 and 59, please replace "though" with --through--

Claim 8, column 12, line 23, please replace "though" with --through--

Signed and Sealed this

Twenty-ninth Day of December, 2009

David J. Kappos
*Director of the United States Patent and Trademark Office*